US012810432B1

(12) United States Patent
Batchelder et al.

(10) Patent No.: US 12,810,432 B1
(45) Date of Patent: Nov. 24, 2026

(54) MEDICAL IMAGE PROCESSING PLATFORM

(71) Applicant: The Joan and Irwin Jacobs Technion-Cornell Institute, New York, NY (US)

(72) Inventors: Kendra Batchelder, New York, NY (US); David Kunz, Beverly Hills, MI (US)

(73) Assignee: The Joan and Irwin Jacobs Technion-Cornell Institute, New York, NY (US)

( * ) Notice: Subject to any disclaimer, the term of this patent is extended or adjusted under 35 U.S.C. 154(b) by 0 days.

(21) Appl. No.: 19/699,071

(22) Filed: Jun. 5, 2026

Related U.S. Application Data

(60) Provisional application No. 63/949,881, filed on Dec. 29, 2025.

(51) Int. Cl.
*G06T 7/00* (2017.01)
*G06K 9/00* (2022.01)
(Continued)

(52) U.S. Cl.
CPC ............ *G06T 7/0016* (2013.01); *G06V 10/25* (2022.01); *G06V 10/40* (2022.01); *G06V 10/764* (2022.01);
(Continued)

(58) Field of Classification Search
USPC ....... 382/100, 103, 128–134, 155, 168, 181, 382/199, 224, 254, 305; 707/723, 758
See application file for complete search history.

(56) References Cited

U.S. PATENT DOCUMENTS 8,065,313 B2 * 11/2011 Yagnik .................. G06F 40/169 707/758
9,858,496 B2 * 1/2018 Sun ..................... G06F 16/5838
(Continued)

FOREIGN PATENT DOCUMENTS

WO 2024086947 A1 5/2024

OTHER PUBLICATIONS

Masroor, “Injecting Private DICOM Tags into Received Instances,” Orthanc Users Forum (Discourse), Jan. 1, 2025, available at https://discourse.orthanc-server.org/t/injecting-private-dicom-tags-into-received-instances/5438 (accessed Jun. 4, 2026).
(Continued)

*Primary Examiner* — Seyed H Azarian
(74) *Attorney, Agent, or Firm* — M&B IP Analysts, LLC

(57) ABSTRACT

A platform, systems, and methods for automated image processing to support analyses such as image-based risk assessment and condition detection. Images acquired from imaging devices are ingested from an archive manager and analyzed using artificial intelligence. The analysis generates scores indicating disease risk, likelihood of a condition, or severity. Results are translated into interoperable outputs and metadata, including risk or likelihood categories, heat-maps, and visual markers such as bounding boxes. New metadata may be efficiently embedded by leveraging unused or blank fields in existing image tags, such as DICOM tags, thereby reducing storage and transmission overhead. Secondary capture images with enriched metadata are archived for longitudinal analysis and future processing. The platform supports risk categorization, visualization, and integration with clinical workflows for applications including, but not limited to, breast cancer risk assessment.

15 Claims, 9 Drawing Sheets

(51) Int. Cl.

| | |
|---|---|
| ***G06V 10/25*** | (2022.01) |
| ***G06V 10/40*** | (2022.01) |
| ***G06V 10/70*** | (2022.01) |
| ***G06V 10/764*** | (2022.01) |
| ***G06V 10/96*** | (2022.01) |
| ***G16H 30/20*** | (2018.01) |
| ***G16H 50/30*** | (2018.01) |

(52) U.S. Cl.

CPC .............. *G06V 10/87* (2022.01); *G06V 10/96* (2022.01); *G16H 30/20* (2018.01); *G16H 50/30* (2018.01); *G06T 2207/20072* (2013.01); *G06T 2207/20081* (2013.01); *G06T 2207/30068* (2013.01); *G06V 2201/03* (2022.01); *G06V 2201/10* (2022.01)

(56) References Cited

U.S. PATENT DOCUMENTS

| | | | | |
|---|---|---|---|---|
| 10,234,394 | B2 | 3/2019 | Chou et al. | |
| 10,622,102 | B2 * | 4/2020 | Itu | A61B 8/0875 |
| 10,702,247 | B2 | 7/2020 | Hare, II et al. | |
| 11,106,716 | B2 | 8/2021 | Bhowan et al. | |
| 11,496,671 | B2 | 11/2022 | Xiong et al. | |
| 11,515,032 | B2 | 11/2022 | Dormer et al. | |
| 11,551,420 | B2 * | 1/2023 | Haslam | G06T 7/0014 |
| 12,001,939 | B2 * | 6/2024 | Hare, II | G16H 30/20 |
| 12,183,452 | B2 * | 12/2024 | Mathur | G16H 30/20 |
| 12,369,883 | B2 | 7/2025 | Bunn | |
| 2016/0307063 | A1 | 10/2016 | Bright et al. | |
| 2019/0205606 | A1 | 7/2019 | Zhou et al. | |
| 2020/0160975 | A1 | 5/2020 | Yao et al. | |
| 2021/0174941 | A1 | 6/2021 | Mathur et al. | |
| 2021/0217486 | A1 * | 7/2021 | Zaaijer | G16B 10/00 |
| 2021/0286997 | A1 | 9/2021 | Lee et al. | |
| 2022/0030175 | A1 | 1/2022 | Powers et al. | |
| 2025/0029707 | A1 | 1/2025 | Park et al. | |

OTHER PUBLICATIONS

International Search Report for PCT application No. PCT/IB2026/055720, dated Oct. 8, 2026. Searching Authority, Israel Patent Office, Jerusalem, Israel.

Written Opinion of the Searching Authority for PCT application No. PCT/IB2026/055720, dated Oct. 8, 2026. Searching Authority, Israel Patent Office, Jerusalem, Israel.

* cited by examiner

MEDICAL IMAGE PROCESSING PLATFORM

CROSS-REFERENCE TO RELATED APPLICATIONS

This application claims the benefit of U.S. Provisional Application No. 63/949,881 filed on Dec. 29, 2025, the contents of which are hereby incorporated by reference.

TECHNICAL FIELD

The present disclosure relates generally to medical image processing, and more specifically to processing medical images from archives in order to make such images more suitable for subsequent processing using artificial intelligence.

BACKGROUND

Medical imaging technology is increasingly being utilized to detect medical conditions and risk factors for developing certain diseases. To this end, many medical images are captured and utilized by medical professionals to diagnose patients.

To accelerate review of medical images and improve the ability to detect certain diseases, conditions, or risk factors, innovations for automatically processing and analyzing medical images have been developed. These innovations allow for detecting conditions faster, more accurately, and more granularly than what human medical professionals can accomplish. With the advancement of artificial intelligence (AI) technology, medical imaging technology is also accelerating at a faster pace.

Medical images may be stored in archives or other systems specially designed for holding medical images and other potentially sensitive data. Medical data is typically subject to regulations which require strict protections for patient data. Accordingly, medical image processing may require additional processing steps as compared to other image analysis processes.

It would therefore be advantageous to provide a solution that would improve efficiency and accuracy of medical image processing.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term “some embodiments” or “certain embodiments” may be used herein to refer to a single embodiment or multiple embodiments of the disclosure.

Certain embodiments disclosed herein include a method. The method comprises: extracting features from an image of a subject, wherein the image has a plurality of tags including a first set of metadata, wherein the plurality of tags includes at least one blank tag; applying an artificial intelligence (AI) model to the extracted features in order to determine at least one risk score for the image, wherein the at least one risk score indicates a risk defined with respect to a condition; generating a secondary capture of the image by inserting a second set of metadata into the at least one blank tag, wherein the secondary capture includes the image and the plurality of tags having the inserted second set of metadata, wherein the second set of metadata includes the at least one risk score.

Certain embodiments disclosed herein also include a non-transitory computer-readable medium having stored thereon causing a processing circuitry to execute a process, the process comprising: extracting features from an image of a subject, wherein the image has a plurality of tags including a first set of metadata, wherein the plurality of tags includes at least one blank tag; applying an artificial intelligence (AI) model to the extracted features in order to determine at least one risk score for the image, wherein the at least one risk score indicates a risk defined with respect to a condition; generating a secondary capture of the image by inserting a second set of metadata into the at least one blank tag, wherein the secondary capture includes the image and the plurality of tags having the inserted second set of metadata, wherein the second set of metadata includes the at least one risk score.

Certain embodiments disclosed herein also include a system. The system comprises: a processing circuitry; and a memory, the memory containing instructions that, when executed by the processing circuitry, configure the system to: extract features from an image of a subject, wherein the image has a plurality of tags including a first set of metadata, wherein the plurality of tags includes at least one blank tag; apply an artificial intelligence (AI) model to the extracted features in order to determine at least one risk score for the image, wherein the at least one risk score indicates a risk defined with respect to a condition; generate a secondary capture of the image by inserting a second set of metadata into the at least one blank tag, wherein the secondary capture includes the image and the plurality of tags having the inserted second set of metadata, wherein the second set of metadata includes the at least one risk score.

Certain embodiments disclosed herein include a method, non-transitory computer-readable medium, or system as noted above or below, further comprising or being configured to perform a process in accordance with the following features: pulling the image from a storage for processing, wherein the features are extracted from the image when the image has been pulled from the storage; and storing the secondary capture in an archive, wherein accessing the image in the storage consumes fewer computing resources than accessing the image in the archive.

Certain embodiments disclosed herein include a method, non-transitory computer-readable medium, or system as noted above or below, further comprising or being configured to perform a process in accordance with the following features: detecting the image as a new image in the storage, wherein the image is pulled from the storage when the image has been detected as a new image.

Certain embodiments disclosed herein include a method, non-transitory computer-readable medium, or system as noted above or below, further comprising or being configured to perform a process in accordance with the following features: wherein the at least one risk score is a plurality of risk scores for respective portions of the image among a plurality of portions of the image, wherein the secondary capture further includes a heatmap of the image, wherein the heatmap includes a plurality of values corresponding to the plurality of risk scores of the respective portions of the image, wherein the plurality of values are based on the plurality of risk scores.

Certain embodiments disclosed herein include a method, non-transitory computer-readable medium, or system as noted above or below, further comprising or being configured to perform a process in accordance with the following features: wherein the at least one risk score is a plurality of risk scores corresponding to respective pixels of the image among a plurality of pixels of the image, further comprising: generating a bounding box for the image based on the plurality of risk scores, wherein the bounding box is generated such that the bounding box surrounds a group of pixels among the plurality of pixels of the image, wherein the pixels of the image among the group are contiguous and have an aggregate risk score above a threshold.

Certain embodiments disclosed herein include a method, non-transitory computer-readable medium, or system as noted above or below, further comprising or being configured to perform a process in accordance with the following features: identifying at least one historical image of the subject based on the image of the subject, wherein the at least one historical image of the subject is associated with historical results data indicating historical analysis results for the at least one historical image; and extracting features from the historical results data, wherein the AI model is further applied to the features extracted from the historical results data.

Certain embodiments disclosed herein include a method, non-transitory computer-readable medium, or system as noted above or below, further comprising or being configured to perform a process in accordance with the following features: determining a type of the image by applying a machine learning model to the features extracted from the image; selecting the AI model from among a plurality of AI models based on the determined type of image, wherein the machine learning model utilizes less processing power than each AI model of the plurality of AI models.

Certain embodiments disclosed herein include a method, non-transitory computer-readable medium, or system as noted above or below, further comprising or being configured to perform a process in accordance with the following features: treating the condition based on the second set of metadata inserted into the plurality of tags of the secondary capture, wherein treating the condition includes determining a status of the condition based on the plurality of risk scores among the second set of metadata.

Certain embodiments disclosed herein include a method, non-transitory computer-readable medium, or system as noted above or below, further comprising or being configured to perform a process in accordance with the following features: wherein each of the at least one blank tag lacks metadata.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
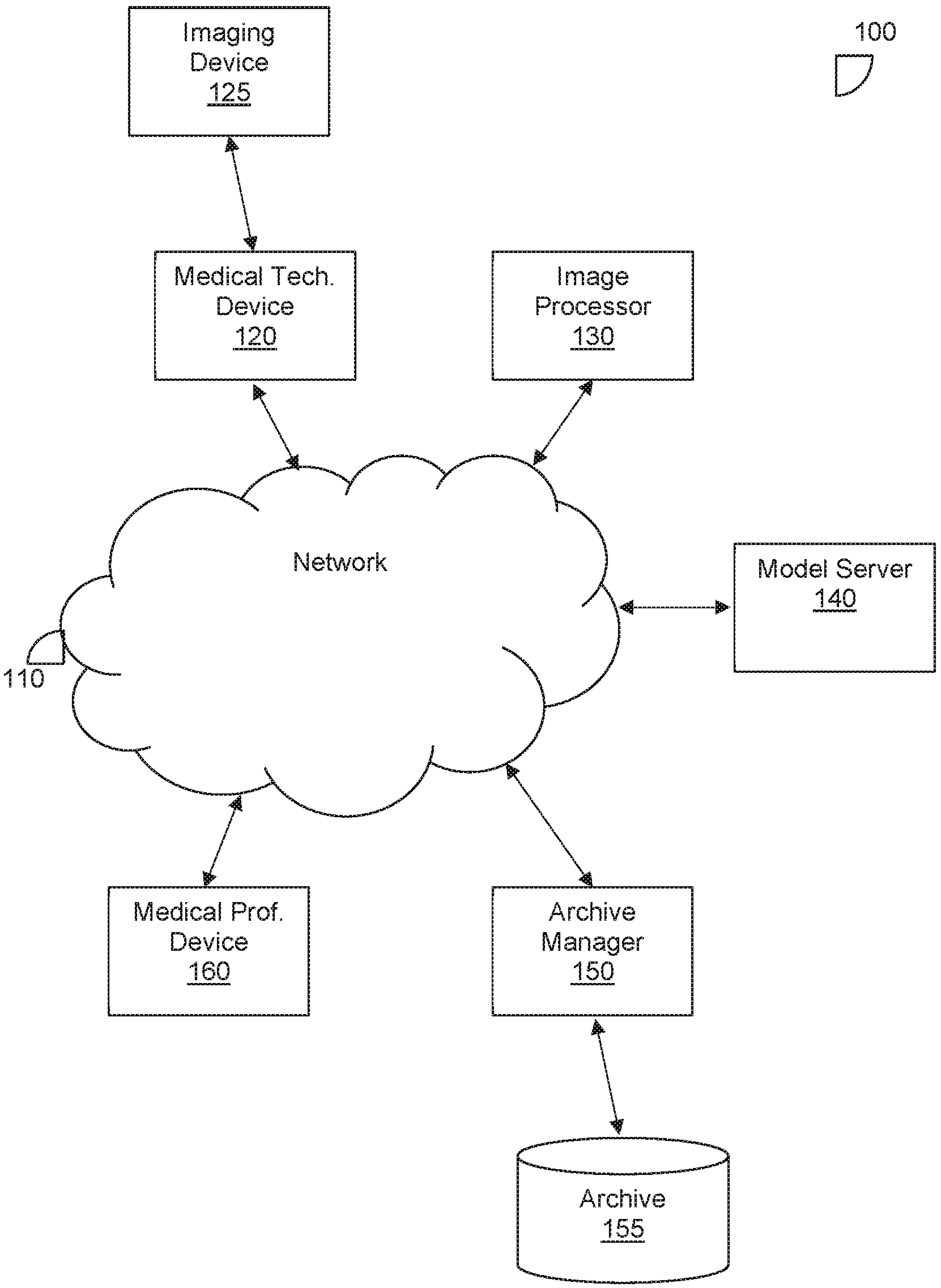
FIG. 1 is a network diagram utilized to describe various disclosed embodiments.

The various disclosed embodiments include a platform for medical image processing as well as methods and systems for image processing. The disclosed embodiments may be utilized to process medical images in order to support image-based risk-assessment for medical conditions such as, but not limited to, breast cancer. Various disclosed embodiments utilize artificial intelligence (AI) to process images and perform analyses such as risk or condition detection analyses based on processed images. To this end, various disclosed embodiments provide techniques for analyzing outputs of machine learning (ML) models or other AI models which are trained to process image data. Such techniques allow for effectively translating results of image processing into forms suitable for subsequent processing.

Various disclosed embodiments utilize an image processor system which is configured to communicate with one or more archive manager systems such as, but not limited to, a picture archiving and communication system (PACS). Such an archive manager system may store images in a digital archive. Images added to the archive may be detected by the image processor via communication with the PACS. When a new image is detected, the new image is pulled for analysis.

The image is analyzed in order to determine one or more scores representing risk of developing one or more conditions (for example, certain diseases), likelihood that the patient has one or more conditions (i.e., condition detection), both, and the like. In an embodiment, analyzing the image includes applying a machine learning model trained to output scores indicating a degree of likelihood, a severity, or a combination thereof, of the condition which is represented in the image. In an embodiment, based on the results of the analysis, the image is tagged with one or more tags. In a further embodiment, the tags include tags indicating a risk category corresponding to a determined score for one or more conditions (for example, a category indicating a risk that the patient has a given condition or that the patient will develop a given condition).

In yet a further embodiment, the tags also include tags indicating characteristics of the image or other meta aspects of the image. Consequently, the tags may effectively be leveraged in order to efficiently introduce new metadata to the images. In this regard, it is noted that medical images stored in formats such as digital imaging and communications in medicine (DICOM) may include a set of tags which leave gaps between tags (for example, providing metadata in every odd-numbered tag and leaving every even-numbered tag blank). Various disclosed embodiments leverage such gaps in tags or other metadata in order to efficiently introduce metadata into images. That is, by leveraging existing tags instead of adding new tags, various disclosed embodiments utilize the storage occupied by the existing tags in order to reduce the amount of storage utilized as contrasted with adding new tags.

Various disclosed embodiments include techniques for risk assessment and condition detection. In particular, various disclosed embodiments detect risks related to certain diseases (for example, that a patient has a certain condition or might develop that condition) such as, but not limited to breast cancer. To this end, in at least some embodiments, the images being processed may be or may include images obtained during a study (for example, 2D digital full field mammography or tomosynthesis, breast MR, breast CT, breast ultrasound, contrast enhanced mammography).

The risk analyses described herein are performed based on results of image processing, and may be further based on contextual data such as, but not limited to characteristics of the subject shown in the medical images (such as age, weight, body mass index [BMI], breast density, etc.).

Various disclosed embodiments may be utilized to provide risk analyses including outputting risk scores corresponding to certain diseases. Such risk analyses may be determined based on configurable thresholds and may categorize risk into categories such as, but not limited to, low, average, intermediate, and high. Outputs of the risk analysis may be provided in interoperable forms such as, but not limited to, digital imaging and communications in medicine (DICOM), health level 7 (HL7), both, and the like.

FIG. 1 shows an example network diagram 100 utilized to describe the various disclosed embodiments. In the example network diagram 100, a medical technician (tech.) device 120, an image processor 130, a model server 140, an archive manager 150, and a medical professional device 160 communicate via a network 110. The network 110 may be, but is not limited to, a wireless, cellular or wired network, a local area network (LAN), a wide area network (WAN), a metro area network (MAN), the Internet, the worldwide web (WWW), similar networks, and any combination thereof.

The medical technician device 120 may be used or operated by a medical technician operating an imaging device 125. The medical technician device 120 may be, but is not limited to, a personal computer, a laptop, a tablet computer, a smartphone, a wearable computing device, or any other device capable of communicating over the network 110.

Such communications may be utilized to, for example but not limited to, to transmit medical images, to receive and display scores, both, and the like. The medical technician device 120 may transmit images captured by one or more cameras to the archive manager 150 for storage in the archive 155. The medical technician device 120 may further transmit data to be used as tags or other metadata stored in association with the images.

The imaging device 125 is configured to capture images. In accordance with various disclosed embodiments, the imaging device 125 may be configured to capture medical images. To that end, the imaging device 125 may be configured to capture medical images created via technologies such as, but not limited to, X-ray, fluoroscopy, computed tomography (CT) scan, magnetic resonance imaging (MRI), ultrasound, sonography, and the like. In certain implementations, the images may be or may include, but are not limited to, 2D digital full field mammography or tomosynthesis, breast MR, breast CT, breast ultrasound, contrast enhanced mammography.

The image processor 130 is configured to process images as described herein. In particular, the image processor 130 is configured to analyze images such as medical images for indicators of risk (for example, risk of developing certain diseases), indicators of conditions (i.e., for detecting diseases or other conditions that the patient shown in the image has), both, and the like.

The image processor 130 is configured to detect and access images stored in the archive 155 in order to pull such images for processing in accordance with various disclosed embodiments. To this end, the image processor 130 may communicate with the archive manager 150 in order to receive data related to incoming images being ingested by the archive manager 150 as well as to pull images for processing from the archive 155.

To aid in processing images, the image processor 130 may include one or more artificial intelligence (AI) models (not shown) such as machine learning models. Such machine learning models may be or may include, but are not limited to, classifier models, regression models, language models (for example, large language models, small language models, etc.), and the like. In accordance with various disclosed embodiments, the image processor 130 is configured to determine a type of image for each image being processed and to determine, based on the type of image, whether to apply one or more AI models, which AI models to apply, both, and the like.

Alternatively, the image processor 130 may communicate with the model server 140, which hosts one or more AI models to be used for processing. Data containing features to be input to one or more AI models may be transmitted to the model server 140 in accordance with various disclosed embodiments. The features may be input to the AI models by the model server 140, thereby applying the AI models to those features.

The archive manager 150 is configured to control access to the archive 155. To this end, the archive manager 150 may be configured to store data (such as, but not limited to, images, tags or other metadata, etc.) in the archive 155, to retrieve data from the archive 155, to send data indicating images being ingested (for example, sending data indicating images in short-term storage to the image processor 130 for use in detecting new images), both, and the like. The archive 155 is a digital archive which stores images and the archive manager 150 may be, but is not limited to, a picture archiving and communication system (PACS).

The medical professional (prof.) device 160 may be used by a medical professional who reviews results of analysis of the image processing results as described herein. To this end, the medical professional device 160 may be, but is not limited to, a personal computer, a laptop, a tablet computer, a smartphone, a wearable computing device, or any other device capable of communicating over the network 110. Such communications may be utilized to, for example but not limited to, to receive and display outputs of the image processor 130 (for example, a dashboard such as the dashboard depicted in FIG. 6 as discussed below).

It should be noted that FIG. 1 depicts an implementation of various disclosed embodiments, but that at least some disclosed embodiments are not necessarily limited as such. Other deployments, arrangements, combinations, and the like, may be equally utilized without departing from the scope of the disclosure.

Figure 2:
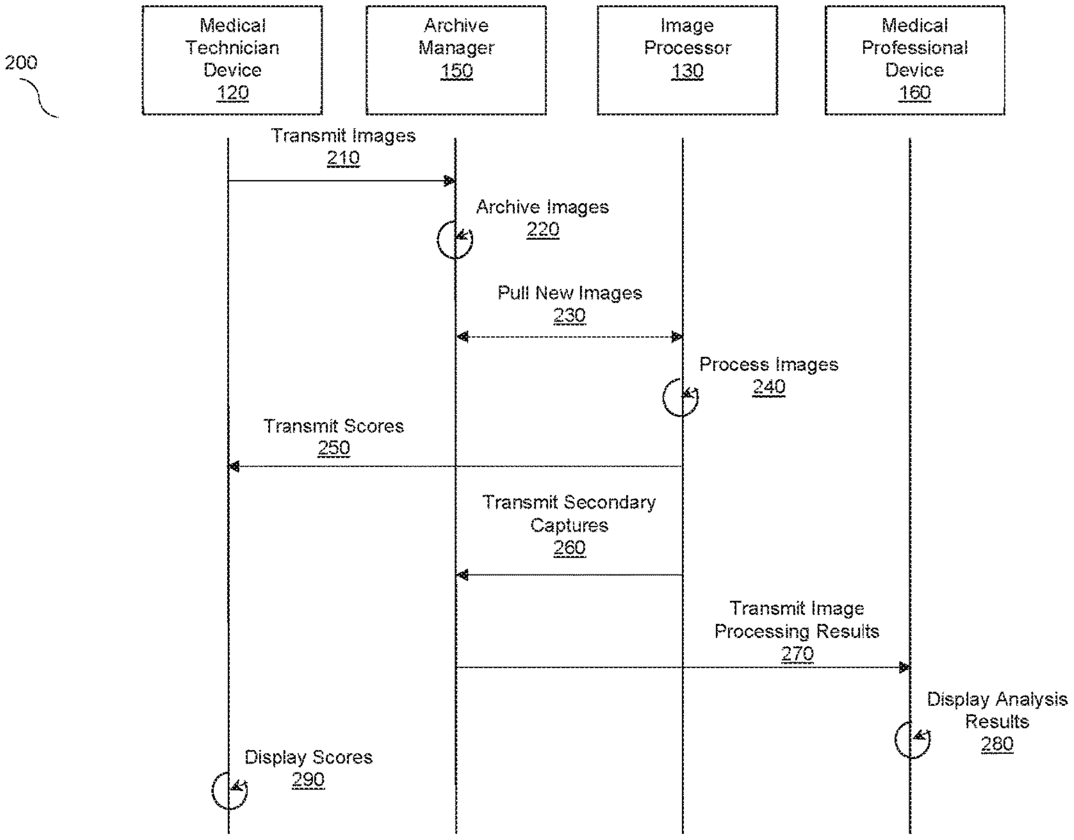
FIG. 2 is a flow diagram illustrating a process for analyzing images stored in an archive which may be utilized in accordance with various disclosed embodiments.

FIG. 2 is a flow diagram 200 illustrating a process for analyzing images stored in an archive which may be utilized in accordance with various disclosed embodiments.

The flow diagram 200 depicts various interactions between and among the medical technician device 120, the image processor 130, the archive manager 150, and the medical professional device 160.

At 210, the medical technician device 120 transmits one or more medical images to be archived to the archive manager 150. As noted above, the images may be accompanied by metadata, for example, metadata in the form of tags. The metadata may indicate, for example but not limited to, characteristics of subjects depicted in the images, circumstances of capture or collection of the image (for example, location of capture, office at which the image was taken, type of device which captured the image, model of device which captured the image, etc.). The metadata may be used as contextual data for image processing and analysis, for example, using the metadata or portions thereof as features input to AI models as discussed below.

At 220, the images are archived by the archive manager 150. In some implementations, the images may be initially received and stored at a short-term storage within the archive manager 150, then eventually migrated to long-term storage within the archive manager 150 and ultimately further migrated to an archive such as the archive 155. The short-term and long-term storage may be utilized to store the images temporarily and allow for efficient access to external systems (such as the image processor 130). That is, by storing the images in temporary storage prior to archiving, the image processor 130 may be able to detect and retrieve images for processing more efficiently than retrieving the images directly from the archive.

At 230, new images detected for the archive are pulled from the archive manager 150 by the image processor 130. The new images may be detected based on data transmitted by the archive manager 150 about images being ingested, and may be pulled, for example, from a short-term storage or otherwise from a temporary storage of the archive manager 150.

At 240, the images are processed by the image processor 130. Processing the images may include, but is not limited to, analyzing the images using artificial intelligence (AI) models and determining scores (for example, risk or detection scores) for the images.

At 250, the scores determined during the image processing are transmitted from the image processor 130 to the medical technician device 120. The scores may be utilized by the medical technician operating the medical technician device 120, stored for subsequent use, or otherwise utilized.

At 260, secondary captures of the images are transmitted from the image processor 130 to the archive manager 150. The secondary captures may be archived by the archive manager 150 and utilized during subsequent processing, for example, during processing of subsequent images. For example, the secondary captures may be utilized as previous images which provide contextual features to improve detection or risk scoring.

In an embodiment, the secondary captures include the images and any metadata of those images. Such metadata includes additional metadata added based on results of the image processing such as, but not limited to, the determined scores. The metadata may also include any original metadata of the image (for example, metadata retrieved via the archive manager 150).

In this regard, a secondary capture may be a derivative image or otherwise a modified version of the image containing additional metadata. In accordance with various disclosed embodiments, the additional metadata is realized as part of the secondary capture by inserting such additional metadata into the blank tags of the image.

At 270, results of the image processing are transmitted from the archive manager 150 to the medical professional device 160. The results may be displayed via the medical professional device 160 or via a display communicatively connected to the medical professional device 160 at 280. The displayed analysis results may be or may include the scores, a visual representation of the scores (for example, a bar showing the score on a scale), and the like.

At 290, the scores may be displayed via the medical technician device 120 or via a display communicatively connected to the medical technician device 120.

Figure 3:
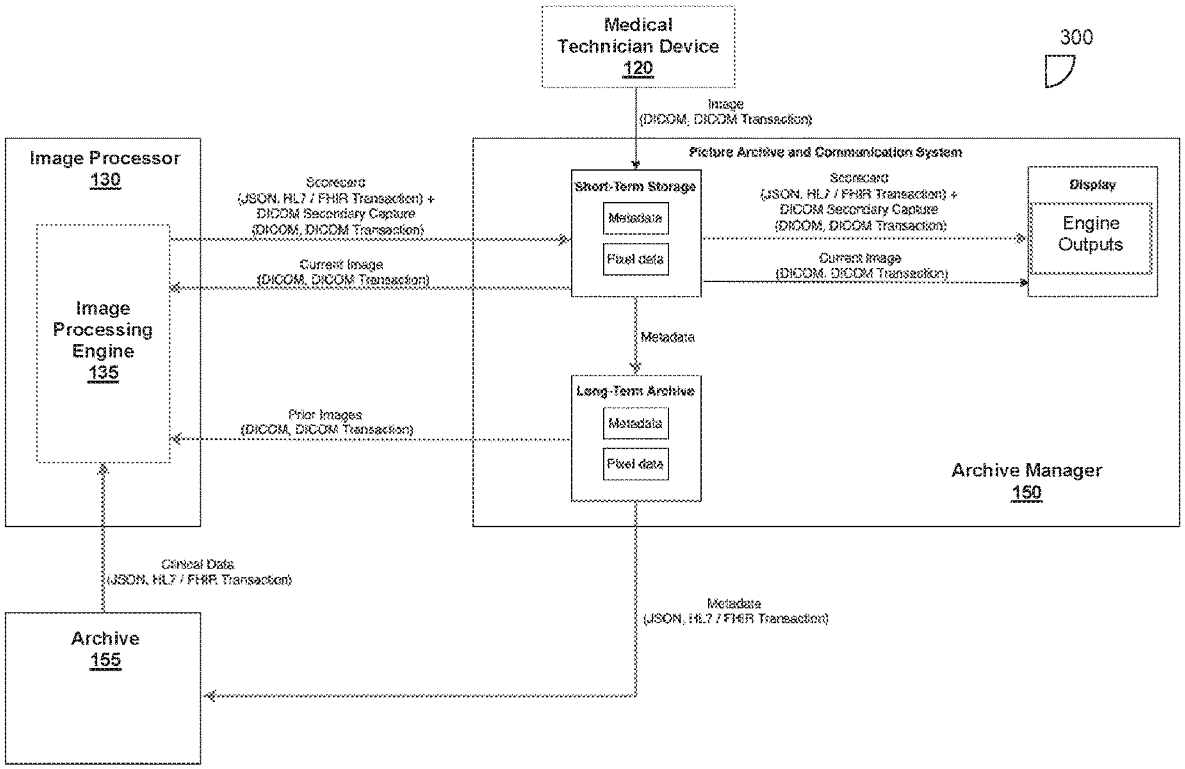
FIG. 3 is a flow diagram illustrating processing image data in accordance with various disclosed embodiments.

FIG. 3 is a flow diagram 300 illustrating processing image data in accordance with various disclosed embodiments.

The flow diagram 300 depicts transmission of data between and among the medical technician device 120, the image processor 130, the archive manager 150, and the archive 155. The archive manager 150 depicted in FIG. 3 is realized as a Picture Archive and Communication System (PACS).

More specifically, the flow diagram 300 depicts an image processing engine 135 running on the image processor 130 extracting a current image from a short-term storage in the archive manager 150. The image processing engine 135 may also extract one or more prior images from a long-term archive in the archive manager 150. Metadata associated with the prior images may have also been sent to the archive 155, and clinical data related to those prior images may be transmitted from the archive 155 to the image processing engine 135.

The image processing engine 135 processes the current image and analyzes the results with respect to the prior images as described herein in order to generate a set of scores (for example, risk scores or other detection scores related to detection of certain conditions, etc.). The image processing engine 135 may transmit a scorecard indicating the scores as well as a secondary capture version of the current image to the short-term storage for storage and eventual archiving. The secondary capture may be or may include the current image, along with metadata of the current image provided by the medical technician device, as well as additional metadata indicating results of the analysis of the processed images. Such additional metadata may be realized as tags, and existing tags which are left blank (for example, as used according to certain formats such as DICOM) may be leveraged for the additional metadata by inserting the additional metadata into the blank tags.

The scorecard and secondary capture stored in the short-term storage may be provided to a display in order to cause display of these engine outputs.

Figure 4:
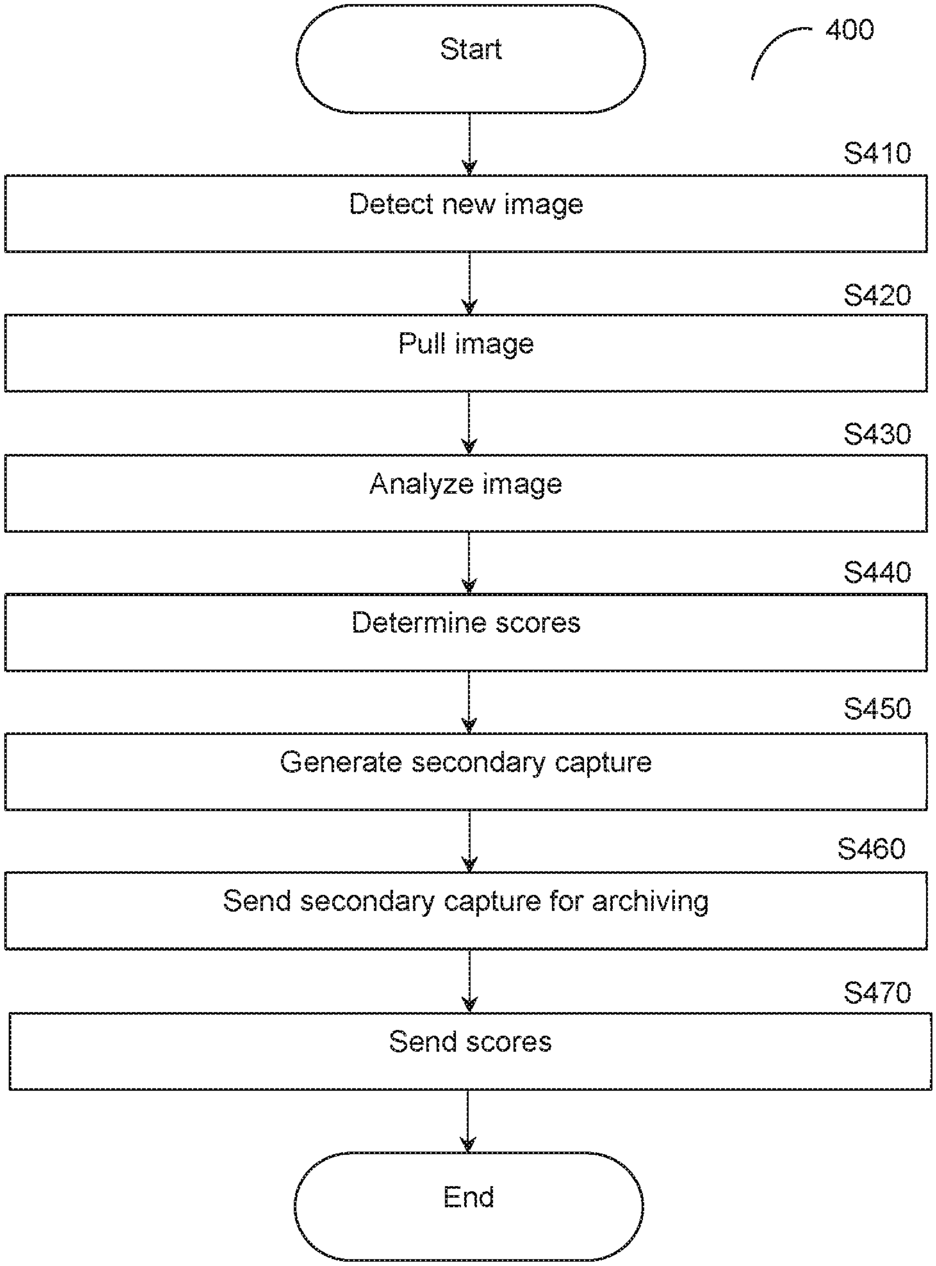
FIG. 4 is a flowchart illustrating a method for analyzing images according to an embodiment.

FIG. 4 is a flowchart 400 illustrating a method for analyzing images according to an embodiment. In an embodiment, the method is performed by the image processor 130.

At S410, a new image is detected. More specifically, a new image is detected with respect to an archive in which the image is or will be stored. In an embodiment, the new image is detected based on data transmitted by an archive manager indicating new images being ingested by the archive manager.

The detected new image may be stored in a short-term storage or otherwise stored temporarily until archived. In this regard, the system performing the method of FIG. 4 may act as a "DICOM listener" or otherwise as an "archive listener" which receives data related to images being provided to a digital archive and detects when to analyze images based on the images being provided to the digital archive.

The image may be, but is not limited to, an image created via a technology such as, but not limited to, X-ray, fluoroscopy, computed tomography (CT) scan, magnetic resonance imaging (MRI) ultrasound, sonography, and the like. In certain implementations, the image may be a 2D digital full field mammography or tomosynthesis, breast MR, breast CT, breast ultrasound, contrast enhanced mammography.

At S420, the detected image is pulled for processing. As noted above, the detected new image may be stored in short-term storage or otherwise stored locally by the archive manager temporarily to allow for more efficient access. Accordingly, identifying the image in such temporary storage and before archiving allows for more efficiently detecting and pulling new images as compared to retrieving the images from an archive. That is, by pulling the images during ingestion by the archive manager, the images may be detected and pulled more efficiently.

To this end, in accordance with certain embodiments, the short-term storage may be configured for fast access or otherwise is configured such that accessing the image in the short-term storage is more efficient than accessing the image in the archive. Such efficiency may be realized via, for example but not limited to, faster retrieval, less processing, lower consumption of network resources (for example, when the short-term storage is locally accessible to the system performing the method of FIG. 4 via direct communication or via one or more local networks and the archive is only accessible via the Internet or other external networks), a combination thereof, and the like.

At S430, the image is analyzed. In an embodiment, analyzing the image includes applying an AI model to a set of features including features extracted from the image, from metadata associated with the image (for example, tags of the image, both, and the like), and the like. In a further embodiment, the AI model is applied to features of one or more previous images, for example features of the previous images, of results of previous processing of the previous images, both, and the like. In some embodiments, a type of the image (for example, a type defined with respect to a body part of a subject shown in the image, with respect to a type of scan, etc.) is determined and utilized to select the AI model to be applied to the image.

An example process for analyzing an image which may be utilized at S430 is described further below with respect to FIG. 5.

At S440, one or more scores are determined based on the image. The scores represent risk of developing one or more conditions (for example, certain diseases), a likelihood that the patient has one or more conditions (i.e., condition detection), both, and the like. The scores may be determined based further on contextual data such as, but not limited to, data indicating characteristics of a subject shown in the image, historical data related to the subject shown in the image (for example, historical results of processing previous images of the subject), both, and the like.

In an embodiment, determining each risk score includes applying a machine learning model trained to output scores indicating a degree of likelihood, a severity, or a combination thereof, of a condition which is represented in the image. Such a machine learning model may be trained to output such scores based on features of processed images used as inputs. In a further embodiment, the machine learning model is further trained to use characteristics of the subject (such as a patient) as features such as, but not limited to, age, weight, body mass index [BMI], breast density, etc.

Such characteristics may be indicated in tags or other metadata associated with the image (as a non-limiting example, DICOM tags) such as, but not limited to, tags stored in association with the image in a digital archive (for example, the archive 155).

At S450, a secondary capture version of the image is generated. In an embodiment, the secondary capture includes the image and a set of tags as associated metadata. The set of tags of the secondary capture includes the first or original tags or other metadata of the image as well as one or more second or new tags. The new tags may be or may include tags generated based on results of analyzing the images such as, but not limited to, the scores determined at S440.

In an embodiment, the new tags introduced to the secondary capture also include tags indicating characteristics of the image or other meta aspects of the image. Such characteristics or meta aspects may include, but are not limited to, a risk category corresponding to a determined score for one or more conditions (for example, a category indicating a risk that the patient has a given condition or a risk that the patient will develop that condition).

In an embodiment, the new tags are created by storing or otherwise inserting new metadata indicating the meta aspects of the image into existing tags. As noted above, medical images may be formatted to include unused or blank tags that lack or otherwise do not include metadata. That is, a blank tag may initially lack metadata but may be populated with new metadata in order to transform the blank tags into the new tags, and likewise an unused tag may initially lack metadata but may be populated with new metadata such that the unused tag becomes a used tag. Accordingly, leveraging these existing tags by inserting metadata into the existing tags allows for introducing metadata to the images more efficiently than creating new tags.

Such secondary captures with metadata inserted into previously blank tags may use less storage space when archived or otherwise stored, require fewer network resources to transmit, and require less computational processing to extract features therefrom. Accordingly, generating a secondary capture by inserting metadata into unused or blank tags allows for generating a secondary capture with a lower total amount of data than by adding new tags, thereby conserving computing resources in generation and storage of such a secondary capture.

In this regard, it is noted that medical images stored in formats such as digital imaging and communications in medicine (DICOM) may include a set of tags which leave gaps between tags (for example, providing metadata in every odd-numbered tag and leaving every even-numbered tag blank). Various disclosed embodiments leverage such gaps in tags or other metadata in order to efficiently introduce metadata into images. That is, by leveraging existing tags instead of adding new tags, various disclosed embodiments utilize the storage occupied by the existing tags in order to reduce the amount of storage utilized as contrasted with adding new tags.

In an embodiment, the secondary capture is or includes a heatmap of the image. Such a heatmap may have values corresponding to different portions of the image, where the values represent different scores or categories of scores (i.e., categories representing degrees of risk or likelihoods of developing certain conditions). When the secondary capture is displayed, the heatmap may be illustrated using colors or other visual markers corresponding to different values or groupings of values (for example, ranges). Accordingly, when the secondary capture is archived, the heatmap may also be archived for subsequent use. Values of the heatmap may also be utilized by applying AI models to features generated based on those values when the AI models are applied to analyze subsequent images showing the same subject in order to further improve the granularity of image analysis.

In a further embodiment, the secondary capture includes one or more bounding boxes or other boundaries. Such boundaries may be lines or other visual markers representing that a certain area within the secondary capture image (for example, a certain group of pixels) represents a notable area within the image. For example, a bounding box may be drawn around or otherwise generated such that the bounding box surrounds a group of pixels which are contiguous and have an aggregate or average score above a threshold (i.e., representing high degree of risk or high likelihood of a given condition). Such bounding boxes may further help illustrate portions of the image to be reviewed by medical professionals. Such an aggregate score may be a sum, average, or other score generated based on multiple base risk scores.

To this end, in yet a further embodiment, the bounding boxes are generated based on the risk scores for the image. For example, when pixels or groups of pixels are assigned risk scores representing a likelihood that the pixel or group of pixels represents a potential indicator of the condition or risk factor for developing the condition. The bounding boxes may be generated in order to surround such a set or group of pixels, for example, when such a set or group of pixels has an aggregate risk score above a threshold (i.e., as determined based on the risk score for each pixel).

Further, in some embodiments, the risk scores may be determined for regions of the image rather than for individual pixels. In such an embodiment, pixels may be assigned the risk scores for their respective regions. That is, all of the pixels within a region having a given risk score may be assigned the risk score for the region. Such an embodiment allows flexibility in controlling the granularity of the AI-based determination of risk scores, which may allow for lower granularity implementations which utilize less computing resources (for example, less resources to apply or train the AI model) or otherwise in order to allow for faster processing.

In another embodiment, generating the secondary capture includes generating a new image file including a copy of the image as well the risk scores for the image. To this end, a new image file containing a copy of the image may be generated, and the risk scores are inserted into the new image file. The new image file with the copy of the image and the risk scores may be saved as a new version of the image file containing the image and may therefore replace the image file containing the image for subsequent use. An example process for generating a secondary capture using a new image file is described further below with respect to FIG. 9.

At S460, the secondary capture is transmitted for archiving. The secondary capture may be sent to an archive manager system configured to store images in an archive, or may otherwise be sent to the archive.

At S470, the scores are sent for subsequent use. In some implementations, the scores may be sent to a user device (for example, the medical professional device 160, the medical technician device 120, or both) to be displayed on that device or on a display that is communicatively connected to the device.

In an embodiment, the scores may be used for diagnosing a patient, treating the patient, or both, with respect to the condition for which the risk scores indicate potential risks. To this end, in a further embodiment, S470 may include diagnosing the patient based on the determined risk scores, treating the patient based on the secondary capture, both, and the like. The course of treatment may be determined based on the representation of the risk shown in the image as indicated by the risk scores. To this end, in a further embodiment, treating the condition includes determining a status of the condition (for example, a stage of progression of the condition or symptoms of the condition) based on the risk scores among the metadata inserted into the blank tags of the secondary capture.

Figure 5:
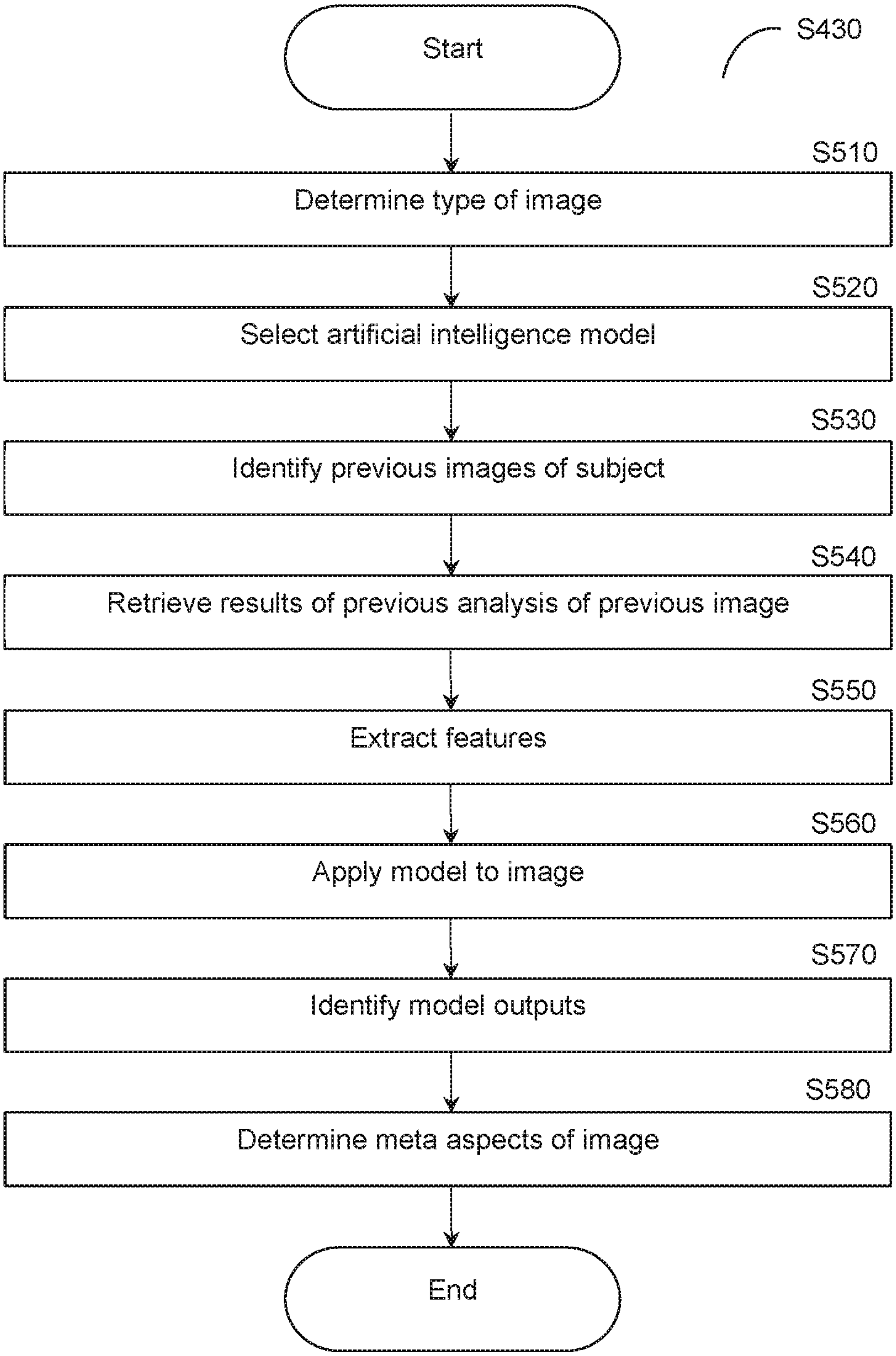
FIG. 5 is a flowchart illustrating a method for processing images for analysis according to an embodiment.

FIG. 5 is a flowchart S430 illustrating a method for processing an image for analysis according to an embodiment.

At S510, a type of image is determined for a current image of a subject. In an embodiment, the image is classified into a type. The type may be defined with respect to, for example but not limited to, a body part shown in the image, a type of scan (for example, mammogram, computed tomography scan, ultrasound, contrast enhanced mammogram, magnetic resonance imaging scan, etc.), a combination thereof, and the like. The type of image may be utilized to select an artificial intelligence model, for example, an AI model trained to generate scores for images of that type. Accordingly, identifying the type of image allows for selecting a suitable artificial intelligence model for subsequent processing.

In an embodiment, the type of image may be determined using machine learning or otherwise using artificial intelligence. To this end, in such an embodiment, S510 includes applying a machine learning model to features extracted from the image in order to output a classification corresponding to a predetermined type of image. Such a machine learning model may be a lighter weight model than the model used during subsequent processing, for example, a model trained on a smaller feature space (i.e., fewer number of features) or otherwise that requires less processing power to apply. This allows for selecting the type of machine learning model to be applied more efficiently.

At S520, an artificial intelligence (AI) model is selected to be applied to features of the image. In an embodiment, the AI model is selected based on the determined type of image.

At optional S530, one or more historical or otherwise previous images of the subject are identified based on the current image. The previous images may be stored in the archive (for example, in an archive storage area), and may be identified based on metadata of images in the archive. For example, metadata of images in the archive may include a tag identifying the subject (for example, by name of patient or unique identification number), and the previous images of the subject may be identified based on a matching identifier between the tag or other metadata identifying the subject in the previous image and in the current image.

At optional S540, results of analyses of the previous images of the subject are retrieved. The results may be utilized, for example, as inputs to one or more AI models used for generating the scores. In this regard, it is noted that certain conditions develop over time, and that historical data for a subject over time may therefore allow for more accurately determining risk or detecting conditions. AI models may be trained based on historical scores or other outputs of previous applications of AI models in order to further refine the models to more accurately generate scores as described herein.

At S550, features are extracted for use as inputs to one or more AI models. In an embodiment, the extracted features include features extracted from the current image. In a further embodiment, the types of features extracted or otherwise the features to be extracted are determined based on the AI model which will be applied to those features (for example, the AI model selected at S520).

In an embodiment, the extracted features further include one or more contextual features extracted from data such as, but not limited to, characteristics of the subject shown in the image, historical analysis results of previous images of the subject (for example, the results retrieved at S540), previous images of the subject, combinations thereof, and the like.

At S560, the AI model is applied to the extracted features. The AI model outputs data indicating scores corresponding to risk, to certain conditions (condition detection), both, and the like. As noted herein, the score may indicate a risk that a patient will develop a condition or a likelihood that the patient has the condition. In some embodiments, the outputs include scores corresponding to different portions of the image (for example, different pixels or groups of pixels). Such scores may effectively represent areas depicted in the image which are indicative of a given condition (i.e., a risk of developing that condition or otherwise a visual indicator of the condition). Scores for different portions of the image may be utilized to generate a heatmap as described herein.

At S570, outputs of the model are identified. In an embodiment, the identified outputs include the scores, and may further include identifying the score for each portion of the image.

At optional S580, one or more meta aspects of the image are determined based on the model outputs. The meta aspects may be or may include, but are not limited to, categories for the scores (for example, categories representing different degrees of risk or likelihoods of a given condition such as high, low, moderate, etc.). The meta aspects may be determined with respect to corresponding portions of the images, for example, portions of the images having respective scores corresponding to those categories. The meta aspects of the image may be utilized to populate metadata of the image during subsequent image processing, for example, as discussed above with respect to FIG. 4.

Figure 6:
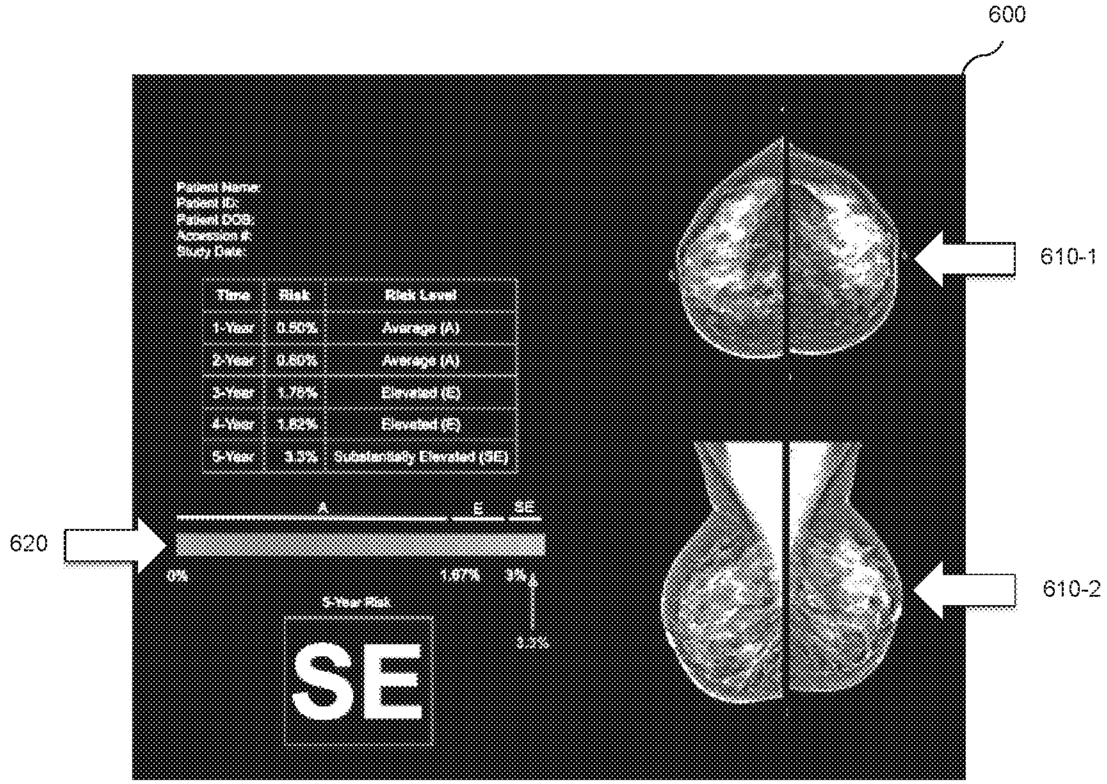
FIG. 6 is an illustration of a risk analysis output in accordance with various disclosed embodiments.

FIG. 6 is an illustration 600 of a risk analysis output in accordance with various disclosed embodiments.

The illustration 600 shows a screenshot of a dashboard. The dashboard displays a set of medical images 610-1 and 610-2 as well as a score bar 620. The score bar 620 displays severity level (for example, low, average, intermediate, or high). In the example implementation shown in FIG. 6, the score bar illustrates a high (H) score (i.e., the score was above a threshold designated for high scores). Accordingly, the dashboard shown in the illustration 600 indicates that the patient whose medical images 610-1 and 610-2 are depicted is at high risk of a condition (for example, breast cancer).

Figure 7:
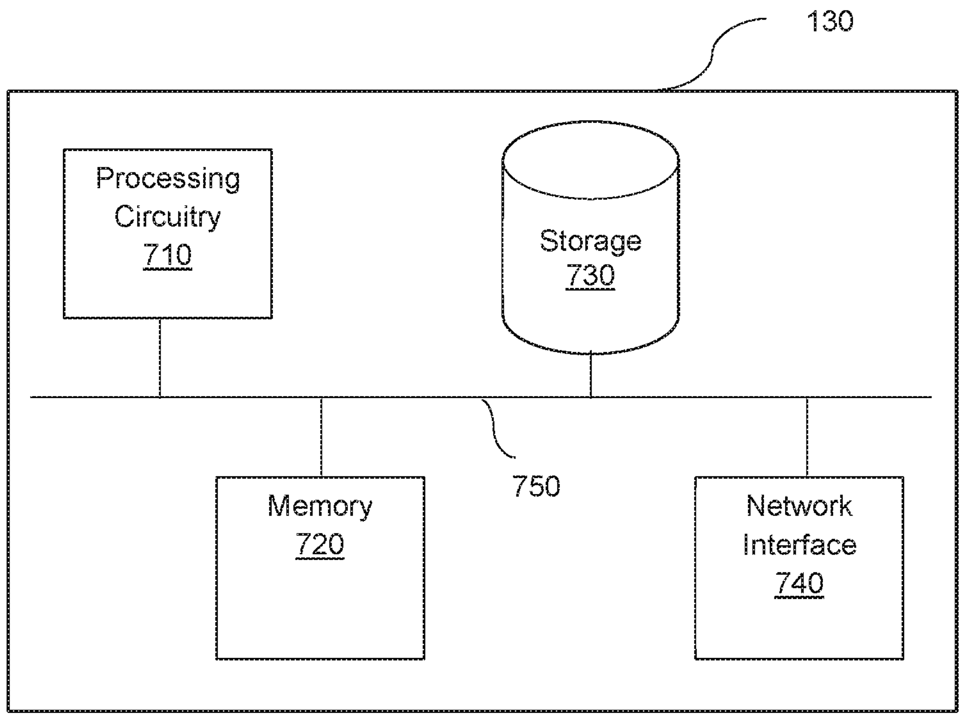
FIG. 7 is a schematic diagram of an image processor according to an embodiment.

FIG. 7 is an example schematic diagram of an image processor 130 according to an embodiment. The image processor 130 includes a processing circuitry 710 coupled to a memory 720, a storage 730, and a network interface 740. In an embodiment, the components of the image processor 130 may be communicatively connected via a bus 750.

The processing circuitry 710 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

In at least some embodiments, the processing circuitry 710 is configured to execute generative artificial intelligence (genAI) models, perform inference using or otherwise apply genAI models, train genAI models, fine-tune genAI models, combinations thereof, and the like. Such genAI models are configured to produce text, images, videos, or other forms of data, and may include, but are not limited to, language models (for example, but not limited to, large language models, small language models, etc.), text-to-image artificial intelligence (AI) image generation systems, text-to-video AI video generators, combinations thereof, and the like. To this end, the processing circuitry 710 may be adapted to realize a transformer deep learning architecture (e.g., a generative pre-trained transformer [GPT], bidirectional encoder representations from transformers [BERT], text-to-text transfer transformer [T5], etc.), a diffusion model, both, and the like.

In accordance with various such embodiments, the hardware utilized for the processing circuitry 710 is selected in order to enable genAI functionality based on factors such as, but not limited to, parallelism (e.g., amounts of parallel processing to be performed), memory demands (e.g., amounts of random access memory [RAM] utilized to store model weights and training during processing or video RAM [VRAM] to support large language models), clock speeds, thread counts, storage (for example, to support certain amounts of storage or storage speeds), cooling (e.g., liquid cooling or air cooling systems), power supply (e.g., in order to enable a target wattage used for certain kinds of activities), networking and connectivity (e.g., in order to support seamless data transfer for deployments involving communications between or among multiple machines or clusters), combinations thereof, and the like.

In embodiments which utilize large language models (LLMs) or otherwise perform operations which may require or be enhanced through use of parallel processing, the processing circuitry 710 may include one or more GPUs or other processing units suitable for parallel processing. Such GPUs may be configured to perform matrix multiplication operations including, but not limited to, performing dot product operations in order to support neural network operations (for example, by performing dot product operations for hidden layer computations) or performing dot product operations in an attention mechanism in order to compute a similarity score between vectors for use in computing attention weights. In at least some such embodiments using GPUs, the processing circuitry 710 may include a number of CPU cores which is equal to or greater than the number of GPUs in order to facilitate or otherwise support parallel processing via multiple GPUs.

The memory 720 may be volatile (e.g., random access memory, etc.), non-volatile (e.g., read only memory, flash memory, etc.), or a combination thereof.

In one configuration, software for implementing one or more embodiments disclosed herein may be stored in the storage 730. In another configuration, the memory 720 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 710, cause the processing circuitry 710 to perform the various processes described herein.

The storage 730 may be magnetic storage, optical storage, and the like, and may be realized, for example, as flash memory or other memory technology, compact disc read-only memory (CD-ROM), Digital Versatile Disks (DVDs), or any other medium which can be used to store the desired information.

The network interface 740 allows the image processor 130 to communicate with other systems, devices, components, applications, or other hardware or software components, for example as described herein.

It should be understood that the embodiments described herein are not limited to the specific architecture illustrated in FIG. 7, and other architectures may be equally used without departing from the scope of the disclosed embodiments.

Figure 8:
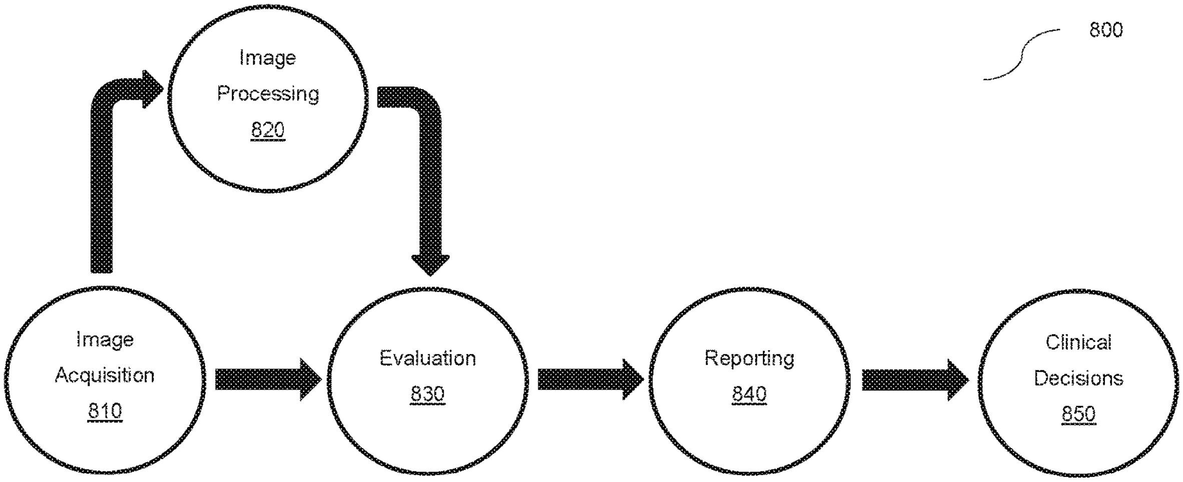
FIG. 8 is a flow diagram illustrating an image-based risk assessment process which may utilize image analysis in accordance with various disclosed embodiments.

FIG. 8 is a flow diagram 800 illustrating an image-based risk assessment process which may utilize image analysis in accordance with various disclosed embodiments.

As depicted in FIG. 8, flow begins with image acquisition 810 in order to obtain images showing a subject such as, but not limited to, a patient. The images acquired at 810 are transmitted for image processing 820 (for example, to the image processor 130 or other system configured to perform the method of FIG. 4). The image processing 820 may include performing image processing as described above, for example, with respect to FIG. 4. In some embodiments, the image processing 820 includes risk scoring or otherwise prioritizing risk for the images.

In the example implementation depicted in FIG. 8, the image acquired at 810 is also transmitted for evaluation 830. The evaluation 830 may be performed by, for example but not limited to, a radiologist or other medical professional trained to assess images for indicators of diseases or other conditions. The evaluation 830 may serve as a complement to the automated image processing 820, for example, by confirming the results or rejecting false positives.

In accordance with various disclosed embodiments, the evaluation 830 may include reviewing a set of images which are prioritized (for example, based on risk scores such as by prioritizing higher risk score images). That is, the images may be displayed or otherwise presented with higher priority images being displayed or presented before lower priority images. Risk scores determined during the image processing 820 may be displayed on or otherwise with the respective images.

Results of the image processing 820 and the evaluation 830 may be utilized to generate reporting 840, which may be reviewed by, for example but not limited to, a doctor or other medical professional trained to diagnose conditions or otherwise to determine a status of a subject shown in the images.

Based on the assessment performed using the reporting 840, clinical decisions 850 are made. The clinical decisions 850 may include, but are not limited to, decisions related to treatment (for example, whether to treat, when to treat, how to treat, etc.), decisions related to further diagnosis (for example, a planned time for next diagnosis or frequency of subsequent diagnoses, additional diagnostic techniques to be performed on the subject, etc.), both, and the like.

Figure 9:
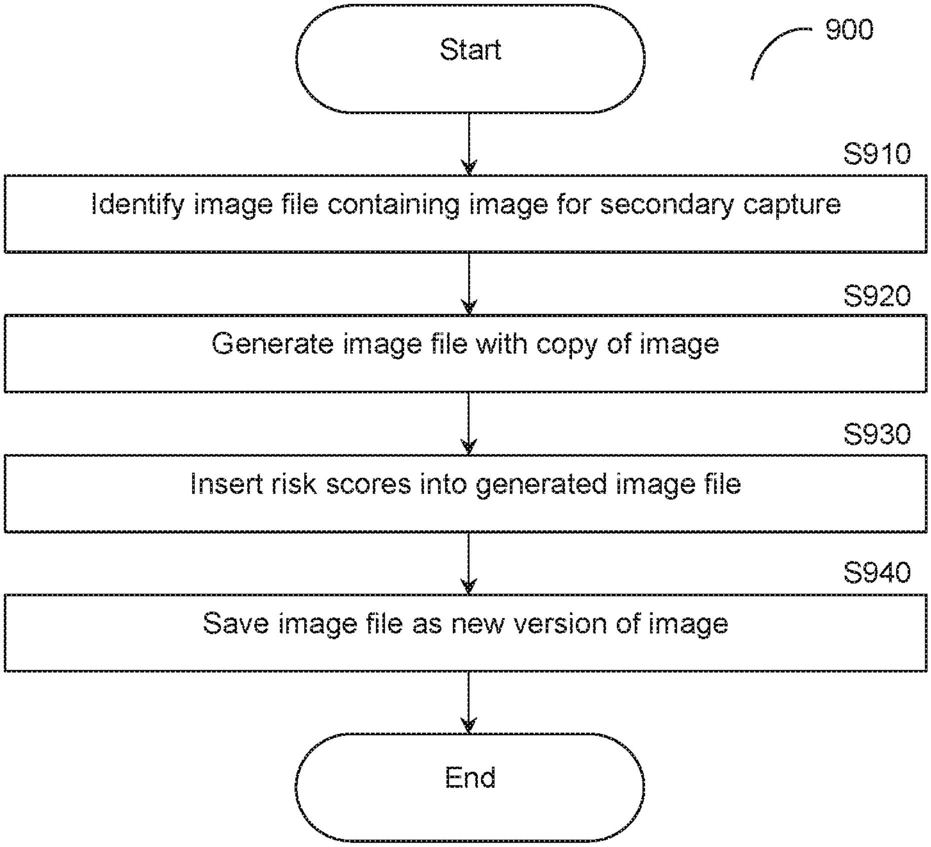
FIG. 9 is a flowchart illustrating a method for generating a secondary capture according to an embodiment.

FIG. 9 is flowchart 900 illustrating a method for generating a secondary capture according to an embodiment. In an embodiment, the method is performed by the image processor 130.

At S910, an image file containing an image is identified to be used for generating a secondary capture. In an embodiment, the identified image file is an image file containing an image for which one or more risk scores have been generated, for example as discussed above with respect to FIG. 4.

At S920, an image file containing a copy of the image is generated.

At S930, one or more risk scores are inserted into the generated image file. The inserted risk scores may be or may include, but are not limited to, risk scores generated for the image that was copied into the image file generated at S920. In an embodiment, the risk scores are generated as described above with respect to FIG. 4.

At S940, the image file containing the copy of the image and the inserted risk scores is saved as a new version of the image. In some embodiments, the new version of the image may replace the existing version of the image. To this end, S940 may include deleting the image file containing the existing version of the image, inserting an identifier of the existing version of the image into the new image file and deleting or modifying the identifier of the image file containing the existing image, and the like. In some embodiments, the new version of the image is saved in short-term storage or otherwise saved temporarily until the new version of the image is archived.

It should be noted that, in some embodiments, the image file containing the new version of the image (for example, the new version with the risk scores inserted therein) may be retained along with the existing image file containing the existing version of the image. This may help, for example, to keep the original in case of corruption during the insertion of the risk scores or saving of the new image file.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various embodiments disclosed herein can be implemented as hardware, firmware, software, or any combination thereof. Moreover, the software may be implemented as an application program tangibly embodied on a program storage unit or computer-readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer-readable medium is any computer-readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for image processing, comprising:

extracting features from a medical image of a subject, wherein the medical image has a plurality of tags including a first set of metadata, wherein the plurality of tags includes at least one blank tag;

applying an artificial intelligence (AI) model to the extracted features in order to determine a plurality of risk scores for respective portions of the medical image among a plurality of portions of the medical image, wherein the plurality of risk scores indicates a risk defined with respect to a condition, wherein the plurality of risk scores correspond to respective pixels of the medical image among a plurality of pixels of the medical image;

generating a bounding box for the medical image based on the plurality of risk scores, wherein the bounding box is generated such that the bounding box surrounds a group of pixels among the plurality of pixels of the image, wherein the pixels of the image among the group are contiguous and have an aggregate risk score above a threshold; and generating a secondary capture of the medical image by inserting a second set of metadata into the at least one blank tag, wherein the secondary capture includes the medical image and the plurality of tags having the inserted second set of metadata, wherein the second set of metadata includes the at least one risk score, wherein the secondary capture further includes a heatmap of the image, wherein the heatmap includes a plurality of values corresponding to the plurality of risk scores of the respective portions of the image, wherein the plurality of values are based on the plurality of risk scores.

2. The method of claim 1, further comprising:

pulling the medical image from a storage for processing, wherein the features are extracted from the medical image when the medical image has been pulled from the storage; and storing the secondary capture in an archive, wherein accessing the medical image in the storage consumes fewer computing resources than accessing the medical image in the archive.

3. The method of claim 2, further comprising:

detecting the medical image as a new medical image in the storage, wherein the medical image is pulled from the storage when the medical image has been detected as a new medical image.

4. The method of claim 1, further comprising:

identifying at least one historical medical image of the subject based on the medical image of the subject, wherein the at least one historical medical image of the subject is associated with historical results data indicating historical analysis results for the at least one historical medical image; and extracting features from the historical results data, wherein the AI model is further applied to the features extracted from the historical results data.

5. The method of claim 1, further comprising:

determining a type of the medical image by applying a machine learning model to the features extracted from the medical image; and selecting the AI model from among a plurality of AI models based on the determined type of medical image, wherein the machine learning model utilizes less processing power than each AI model of the plurality of AI models.

6. The method of claim 1, further comprising:

treating the condition based on the second set of metadata inserted into the plurality of tags of the secondary capture, wherein treating the condition includes determining a status of the condition based on the plurality of risk scores among the second set of metadata.

7. The method of claim 1, wherein each of the at least one blank tag lacks metadata.

8. A non-transitory computer-readable medium having stored thereon instructions for causing a processing circuitry to execute a process, the process comprising:

extracting features from a medical image of a subject, wherein the medical image has a plurality of tags including a first set of metadata, wherein the plurality of tags includes at least one blank tag;

applying an artificial intelligence (AI) model to the extracted features in order to determine a plurality of risk scores for respective portions of the medical image among a plurality of portions of the medical image, wherein the plurality of risk scores indicates a risk defined with respect to a condition, wherein the plurality of risk scores correspond to respective pixels of the medical image among a plurality of pixels of the medical image;

generating a bounding box for the medical image based on the plurality of risk scores, wherein the bounding box is generated such that the bounding box surrounds a group of pixels among the plurality of pixels of the image, wherein the pixels of the image among the group are contiguous and have an aggregate risk score above a threshold; and generating a secondary capture of the medical image by inserting a second set of metadata into the at least one blank tag, wherein the secondary capture includes the medical image and the plurality of tags having the inserted second set of metadata, wherein the second set of metadata includes the at least one risk score, wherein the secondary capture further includes a heatmap of the image, wherein the heatmap includes a plurality of values corresponding to the plurality of risk scores of the respective portions of the image, wherein the plurality of values are based on the plurality of risk scores.

9. A system for image processing, comprising:

a processing circuitry; and a memory, the memory containing instructions that, when executed by the processing circuitry, configure the system to:

extract features from a medical image of a subject, wherein the medical image has a plurality of tags including a first set of metadata, wherein the plurality of tags includes at least one blank tag;

apply an artificial intelligence (AI) model to the extracted features in order to determine a plurality of risk scores for respective portions of the medical image among a plurality of portions of the medical image, wherein the plurality of risk scores indicates a risk defined with respect to a condition, wherein the plurality of risk scores correspond to respective pixels of the medical image among a plurality of pixels of the medical image;

generate a bounding box for the medical image based on the plurality of risk scores, wherein the bounding box is generated such that the bounding box surrounds a group of pixels among the plurality of pixels of the image, wherein the pixels of the image among the group are contiguous and have an aggregate risk score above a threshold; and generate a secondary capture of the medical image by inserting a second set of metadata into the at least one blank tag, wherein the secondary capture includes the medical image and the plurality of tags having the inserted second set of metadata, wherein the second set of metadata includes the at least one risk score, wherein the secondary capture further includes a heatmap of the image, wherein the heatmap includes a plurality of values corresponding to the plurality of risk scores of the respective portions of the image, wherein the plurality of values are based on the plurality of risk scores.

10. The system of claim 9, wherein the system is further configured to:

pull the medical image from a storage for processing, wherein the features are extracted from the medical image when the medical image has been pulled from the storage; and store the secondary capture in an archive, wherein accessing the medical image in the storage consumes fewer computing resources than accessing the medical image in the archive.

11. The system of claim 10, wherein the system is further configured to:

detect the medical image as a new medical image in the storage, wherein the medical image is pulled from the storage when the medical image has been detected as a new medical image.

12. The system of claim 9, wherein the system is further configured to:

identify at least one historical medical image of the subject based on the image of the subject, wherein the at least one historical medical image of the subject is associated with historical results data indicating historical analysis results for the at least one historical medical image; and extract features from the historical results data, wherein the AI model is further applied to the features extracted from the historical results data.

13. The system of claim 9, wherein the system is further configured to:

determine a type of the medical image by applying a machine learning model to the features extracted from the medical image; and select the AI model from among a plurality of AI models based on the determined type of medical image, wherein the machine learning model utilizes less processing power than each AI model of the plurality of AI models.

14. The system of claim 9, wherein the system is further configured to:

treat the condition based on the second set of metadata inserted into the plurality of tags of the secondary capture, wherein treating the condition includes determining a status of the condition based on the plurality of risk scores among the second set of metadata.

15. The system of claim 9, wherein each of the at least one blank tag lacks metadata.

* * * * *